United States Patent
Kashiwagi et al.

(10) Patent No.: US 6,756,458 B2
(45) Date of Patent: Jun. 29, 2004

(54) FLUORINATED COMPOUND, METHOD FOR ITS PRODUCTION AND POLYMER THEREOF

(75) Inventors: Kimiaki Kashiwagi, Kanagawa (JP); Gen Ogawa, Kanagawa (JP); Masakuni Sato, Kanagawa (JP); Kazuya Oharu, Kanagawa (JP); Isamu Kaneko, Kanagawa (JP); Norihide Sugiyama, Kanagawa (JP); Shin Tatematsu, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/307,392

(22) Filed: Dec. 2, 2002

(65) Prior Publication Data

US 2003/0125490 A1 Jul. 3, 2003

Related U.S. Application Data

(63) Continuation of application No. PCT/JP01/04523, filed on May 30, 2001.

(30) Foreign Application Priority Data

May 31, 2000 (JP) ........................................ 2000-161714

(51) Int. Cl.[7] .............................................. C08F 136/16
(52) U.S. Cl. .................... 526/252; 526/72; 526/247; 526/253; 568/683; 568/685
(58) Field of Search ............................. 526/53, 347, 72, 526/252; 568/683, 685

(56) References Cited

U.S. PATENT DOCUMENTS

| | | | |
|---|---|---|---|
| 3,391,119 A | 7/1968 | Anderson | |
| 4,897,457 A | 1/1990 | Nakamura et al. | |
| 4,910,276 A | 3/1990 | Nakamura et al. | |
| 5,260,492 A | 11/1993 | Feiring et al. | |
| 5,350,821 A | 9/1994 | Feiring et al. | |
| 5,475,071 A * | 12/1995 | Smart et al. | 526/252 |
| 5,502,132 A | 3/1996 | Sugiyama et al. | |
| 5,510,406 A | 4/1996 | Matsuo et al. | |
| 5,760,139 A | 6/1998 | Koike et al. | |
| 5,783,636 A | 7/1998 | Koike et al. | |
| 5,916,971 A | 6/1999 | Koike et al. | |
| 6,071,441 A | 6/2000 | Koganezawa et al. | |
| 6,111,062 A | 8/2000 | Shirota et al. | |
| 6,166,125 A * | 12/2000 | Sugiyama et al. | 524/462 |
| 6,201,085 B1 | 3/2001 | Matsukura et al. | |
| 6,221,987 B1 | 4/2001 | Sugiyama | |
| 6,225,382 B1 | 5/2001 | Matsukura et al. | |
| 6,271,312 B1 | 8/2001 | Koike et al. | |
| 6,284,379 B1 | 9/2001 | Matsukura et al. | |
| 6,337,379 B2 | 1/2002 | Matsukura et al. | |
| 6,448,452 B2 | 9/2002 | Kashiwagi et al. | |
| 6,670,511 B2 * | 12/2003 | Kashiwagi et al. | 568/683 |

FOREIGN PATENT DOCUMENTS

| | | | |
|---|---|---|---|
| EP | 303292 | * | 2/1989 |
| EP | 0 303 292 | | 2/1989 |
| EP | 907088 | * | 4/1999 |
| EP | 0 907 088 | | 4/1999 |
| JP | 44-2963 | | 2/1944 |
| JP | 01-131214 | | 5/1989 |
| JP | 1-131215 | | 5/1989 |
| JP | 01-131215 | | 5/1989 |
| JP | 1-143843 | | 6/1989 |
| JP | 08-5848 | | 1/1996 |
| JP | 8-334633 | | 12/1996 |

OTHER PUBLICATIONS

Milos Hudlicky, "Chemistry of Organic Flourine Compounds", Pergamon Press, (1961).

* cited by examiner

*Primary Examiner*—David W. Wu
(74) *Attorney, Agent, or Firm*—Oblon, Spivak, McClelland, Maier & Neustadt, P.C.

(57) ABSTRACT

A novel polymer useful as an optical resin material excellent in heat resistance, a novel monomer for obtaining the polymer, etc., are provided. A fluorinated diene represented by $CF_2=CF(CF_2)_nC(CF_3)ROCF=CF_2$ (wherein R is a fluorine atom or a trifluoromethyl group, and n is an integer of from 1 to 3), and a polymer thereof.

10 Claims, No Drawings

FLUORINATED COMPOUND, METHOD FOR ITS PRODUCTION AND POLYMER THEREOF

TECHNICAL FIELD

The present invention relates to a fluorinated diene having two unsaturated bonds, a method for its production and a polymer thereof.

BACKGROUND ART

As a fluorinated diene having two carbon—carbon unsaturated double bonds (hereinafter referred to as unsaturated bonds), $CF_2=CF(CF_2)_kOCF=CF_2$ (wherein k is an integer of from 1 to 3) has been known (JP-A-1-14843). By cyclopolymerization of this compound, an amorphous polymer can be obtained, and such a polymer has high elastic modulus, yield and breaking extension and is tough and excellent in impact resistance. Further, its transparency is also high, and it can be used for an optical material such as optical fiber or optical waveguide. However, it has a drawback that when this polymer is used to make an optical material, the glass transition temperature (Tg) is low, and if it is used at a high temperature for a long period of time, the optical properties will change. Accordingly, it has been desired to develop a base material having a higher Tg.

It is an object of the present invention to provide a polymer which maintains the mechanical properties which the above amorphous polymer has, and has a higher glass transition temperature, so that it can be an optical resin material excellent in heat resistance, and to provide a fluorinated diene having two unsaturated bonds, which is capable of presenting such a polymer.

DISCLOSURE OF THE INVENTION

The present invention is the following invention relating to a fluorinated diene represented by the formula 1, a method for its production and a polymer thereof.

A fluorinated diene represented by the formula 1.

A method for producing a fluorinated diene represented by the formula 1, which comprises dehalogenating $Z^1$ and $Z^2$ of a fluorinated compound represented by the formula 2.

A polymer comprising monomer units formed by polymerization of a fluorinated diene represented by the formula 1.

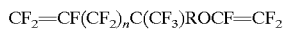

$CF_2=CF(CF_2)_nC(CF_3)ROCF=CF_2$   Formula 1

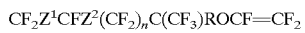

$CF_2Z^1CFZ^2(CF_2)_nC(CF_3)ROCF=CF_2$   Formula 2 wherein R is a fluorine atom or a trifluoromethyl group, each of $Z^1$ and $Z^2$ which are independent of each other, is a halogen atom other than a fluorine atom, and n is an integer of from 1 to 3.

BEST MODE FOR CARRYING OUT THE INVENTION

The fluorinated diene represented by the formula 1 can be obtained by dehalogenating $Z^1$ and $Z^2$ of the fluorinated compound represented by the formula 2. Each of $Z^1$ and $Z^2$ which are independent of each other, is a halogen atom other than a fluorine atom, preferably a chlorine atom or a bromine atom, and particularly preferably, each is a chlorine atom. By the dehalogenation of these halogen atoms, a double bond will be formed, and a fluorinated diene represented by the formula 1 will be formed.

The dehalogenation is carried out by having a dehalogenating agent acted in a polar solvent. The dehalogenating agent is a reaction agent having a function to act on halogen atoms in a substrate thereby to withdraw the halogen atoms. As such a dehalogenating agent, zinc, sodium, magnesium, tin, copper, iron or other metals are preferred. From the viewpoint of such a reaction condition that a relatively low reaction temperature can be employed, zinc is preferred as such a dehalogenating agent. As the polar solvent, an organic polar solvent such as dimethylformamide, 1,4-dioxane, diglyme or methanol, or water, may, for example, be preferably employed.

The molar ratio of the dehalogenating agent to the fluorinated compound represented by the formula 2, is preferably from 1 to 10 times, more preferably from 2 to 3 times. The reaction temperature is usually from 40 to 100° C., preferably from 50 to 70° C. Usually, the reaction is carried out by dropwise adding the fluorinated compound represented by the formula 2, in the presence of the dehalogenating agent and the solvent, and isolation of the reaction product is carried out by withdrawing the reaction product from the reaction system by distillation promptly after the reaction.

The fluorinated compound represented by the formula 2 is a novel compound, and a compound (formula 2-1) wherein R is a fluorine atom, can be produced, for example, from a known fluorinated compound represented by the formula 3-1. Further, a fluorinated compound (formula 2-2) represented by the formula 2 wherein R is a trifluoromethyl group, can be produced, for example, from a known fluorinated compound represented by the formula 4-1.

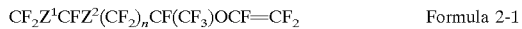

$CF_2Z^1CFZ^2(CF_2)_nCF(CF_3)OCF=CF_2$   Formula 2-1

$CF_2Z^1CFZ^2(CF_2)_nCF=CF_2$   Formula 3-1

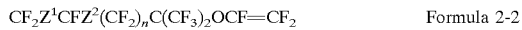

$CF_2Z^1CFZ^2(CF_2)_nC(CF_3)_2OCF=CF_2$   Formula 2-2

$CF_2Z^1CFZ^2(CF_2)_nCOF$   Formula 4-1

Firstly, a method for producing the fluorinated compound represented by the formula 2-1 will be described. The unsaturated group in the fluorinated compound represented by the formula 3-1 is epoxidized to an epoxy compound (formula 3-2), and this epoxy compound is isomerized and converted to a fluorinated ketone compound (formula 3-3). To this fluorinated ketone compound, hexafluoropropylene oxide is added to obtain a fluorinated ether compound (formula 3-4), and then, the fluorinated ether compound is pyrolyzed to obtain a fluorinated compound (formula 2-1) represented by the formula 2 wherein R is a fluorine atom.

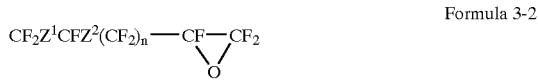

Formula 3-2

Formula 3-3

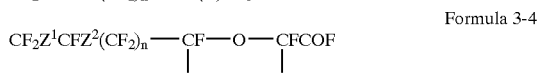

Formula 3-4

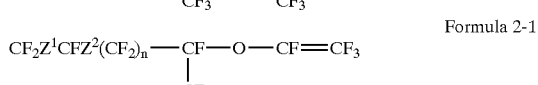

Formula 2-1

For the production of the epoxy compound (formula 3-2), it is possible to apply a method of employing oxygen as disclosed in "Chemistry of organic fluorine compound", 1962 edition, pp. 168–169, edited by Hudlicky, a method of employing hydrogen peroxide as disclosed in JP-B-44-2963, or a method of employing a hypochlorite aqueous solution in the presence of a phase-transfer catalyst.

Particularly preferred is a method of employing a sodium hypochlorite aqueous solution in the presence of a phase-transfer catalyst.

In the case of the method of employing a hypochlorite aqueous solution, the reaction temperature is at least the melting point of the hypochlorite aqueous solution, usually within a range of from −20 to 60° C., preferably from −20 to 30° C., although it may vary depending upon the phase-transfer catalyst to be used or its amount. The amount of the phase-transfer catalyst is preferably from 0.01 to 20 mass %, particularly preferably from 0.05 to 10 mass %, based on the compound represented by the formula 3-1. As the hypochlorite, an alkali metal salt or an alkaline earth metal salt, such as NaClO, KClO, Ca(ClO)$_2$ or NaBrO, may be mentioned. From the industrial viewpoint, use of NaClO is preferred. The effective concentration of the hypochlorite in the hypochlorite aqueous solution is preferably from 1 to 20 mass %.

As the phase-transfer catalyst, a quaternary ammonium salt, a quaternary phosphonium salt, a quaternary arsonium salt, a sulfonium salt or a crown ether, known as a phase-transfer catalyst, may, for example, be used. Among them, a quaternary ammonium salt and a quaternary phosphonium salt are preferred. As an organic group to be bonded to the nitrogen atom or the phosphorous atom, an alkyl group, an aryl group or an aralkyl group may, for example, be preferred, and as an anion, a halogen ion such as a chlorine ion, or a mineral acid ion such as a sulfate ion, is preferred. A particularly preferred phase-transfer catalyst is a tetraalkylammonium salt.

The epoxy compound (formula 3-2) is subjected to an isomerization reaction in a gas phase or in a liquid phase using a metal compound such as a metal oxide, a metal oxyhalide or a metal halide as a catalyst, whereby a fluorinated ketone compound (formula 3-3) can be obtained. As the metal component of the catalyst, Al, Zr, Ti, Fe, Co, Ni or Cr may, for example, be mentioned, and particularly preferred is aluminum. A reaction wherein a fluorinated epoxide is isomerized in the presence of a catalyst such as aluminum oxide or aluminum chloride to obtain a fluorinated ketone, is known and is disclosed, for example, in U.S. Pat. No. 3,391,119.

In the present invention, when the above isomerization reaction is carried out in a gas phase, a metal oxide catalyst such as γ-alumina can be used as the catalyst. However, a more preferred catalyst is a metal oxyhalide. For example, a metal oxyhalide obtainable by activating the above-mentioned metal oxide or multiple metal oxide with a fluorocarbon, is preferred. As the fluorocarbon, a chlorofluorocarbon such as trichlorotrifluoroethane, chlorodifluoromethane, trichlorofluorometane or dichlorodifluoromethane, may, for example, be mentioned.

The isomerization reaction in the gas phase method is carried out by contacting a gas of the epoxy compound (formula 3-2) to the above-mentioned catalyst. The gas of the epoxy compound may be used for the reaction as diluted with an inert gas such as nitrogen gas. The reaction temperature is preferably at least a temperature at which the epoxy compound is vaporized, particularly from 100 to 300° C.

In the present invention, when the above-mentioned isomerization reaction is carried out in a liquid phase, the above-mentioned metal oxyhalide or the above-mentioned metal halide can be used as the catalyst. The metal halide is preferably one activated by the fluorocarbon in the same manner as mentioned above. As the solvent, an inert solvent such as a fluorinated solvent, an ether type solvent or an aprotic polar solvent. It is also possible to use as a solvent the liquid fluorocarbon employed for activating the catalyst, as it is. The amount of the catalyst is preferably from 0.005 to 20 mol %, particularly preferably from 0.1 to 10 mol %, based on the epoxy compound (formula 3-2). The reaction temperature is preferably from −20 to +150° C., particularly preferably from 20 to 40° C.

Further, as the above-mentioned ether type solvent, diethyl ether, methyl tert-butyl ether, dimethoxy ethane, tetrahydrofuran, dioxane, monoglyme, diglyme, triglyme or tetraglyme, may, for example, be mentioned. As the above-mentioned aprotic polar solvent, acetonitrile, benzonitrile, sulfolane, dimethylacetamide or dimethylsulfoxide, may, for example, be mentioned. These solvents may also be used as the ether type solvent or the aprotic polar solvent which will appear in the following description.

In a solvent, a metal fluoride is acted on the fluorinated ketone compound (formula 3-3), followed by a reaction with hexafluoropropylene oxide to obtain a fluorinated ether compound (formula 3-4). The reaction temperature is preferably at most 50° C., particularly preferably from 5 to 25° C. As the metal fluoride, potassium fluoride, cesium fluoride or sodium fluoride, may, for example, be mentioned. As the solvent for the reaction, an ether type solvent or an aprotic polar solvent is preferred. The reaction pressure of hexafluoropropylene oxide is suitably from 0 to 1 MPa, and preferably, a pressure of from 0.1 to 0.5 MPa is used.

The fluorinated ether compound (formula 3-4) is pyrolized to obtain a fluorinated compound (formula 2-1) of the formula 2 wherein R is a fluorine atom. The pyrolysis may, of course, be carried out by directly pyrolizing the fluorinated ether compound, or the fluorinated ether compound may firstly be converted to an alkali salt of the corresponding carboxylic acid and then hydrolyzed. Further, the fluorinated ether compound (formula 3-4) has an active group (—COF), and after converting such an active group to a group stable in handling, it may be converted to the alkali salt of the carboxylic acid. For example, it may be reacted with an alkanol to form an alkyl ester of the corresponding carboxylic acid, which is then converted to the alkali salt.

In a case where the fluorinated ether compound is directly pyrolized, it is preferred that the fluorinated ether compound is gasified and, if necessary, diluted with an inert gas such as nitrogen gas, followed by contacting it with a solid basic salt or glass beads at a high temperature. The temperature for the pyrolysis is preferably from 200 to 500° C., particularly preferably from 250 to 350° C. As the solid basic salt, sodium carbonate, potassium carbonate or sodium phosphate may, for example, be used, and particularly preferred is sodium carbonate.

The fluorinated ether compound (formula 3-4) may be reacted with an alkali metal hydroxide to form an alkali metal salt of the corresponding carboxylic acid. This alkali metal salt may be pyrolized at from 100 to 300° C., preferably from 150 to 250° C. to obtain the desired fluorinated compound. It is preferred to use this alkali metal salt pyrolytic method, since as compared with the above-mentioned gas phase pyrolytic method, the pyrolysis can be carried out at a low temperature, and the yield is also high. Further, it is preferred that the production of the alkali metal salt is carried out by using water or an alcohol as the solvent, and the obtained alkali metal salt is pyrolyzed after being sufficiently dried. Further, as the alkali metal salt, a sodium salt or a potassium salt may be mentioned, but a potassium salt is preferred since the pyrolysis can be carried out at a lower temperature.

Now, a method for producing the fluorinated compound (formula 2-2) from the fluorinated compound represented by the formula 4-1, will be described. Two trifluoromethyl groups are introduced to the carbon atom of a carbonyl group of the fluorinated compound represented by the formula 4-1 to obtain a fluorinated alcohol (formula 4-2), and to this fluorinated alcohol, hexafluoropropylene oxide is added to obtain a fluorinated ether compound (formula 4-3), and then, this fluorinated ether compound is pyrolyzed to obtain the fluorinated compound represented by the formula 2-2.

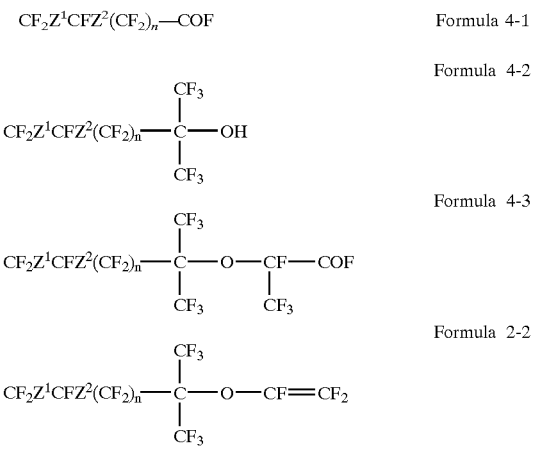

As a method for introducing two trifluoromethyl groups to the carbon atom of the carbonyl group of the fluorinated compound represented by the formula 4-1, a method of reacting trifluoromethyl trimethylsilane to the fluorinated compound represented by the formula 4-1 in a polar solvent in the presence of a metal fluoride or an ammonium fluoride salt, is preferred. As the metal fluoride, an alkali metal fluoride such as potassium fluoride, cesium fluoride or sodium fluoride, is preferred. Further, as the ammonium fluoride salt, tetrabutylammonium fluoride is preferred. The amount of the metal fluoride or the ammonium fluoride salt to the fluorinated compound represented by the formula 4-1 is preferably from 2 to 3 times by mol, and the amount of trifluoromethyl trimethylsilane to the fluorinated compound represented by the formula 4-1 is preferably from 2 to 2.5 times by mol. The temperature for the reaction is suitably at most 30° C., preferably from −78 to +15° C. As the polar solvent, the above-mentioned ether type solvent or the aprotic solvent may be mentioned, and particularly preferred is tetrahydrofuran or acetonitrile.

By the above-mentioned reaction employing the metal fluoride, a metal alkoxide of the fluorinated alcohol (formula 4-2) is obtained. This alkoxide is treated with an acid to obtain a fluorinated alcohol. As such an acid, concentrated sulfuric acid, diluted sulfuric acid, concentrated hydrochloric acid or diluted hydrochloric acid may, for example, be preferably employed. Further, this metal alkoxide may be supplied for the subsequent reaction without converting it to the fluorinated alcohol. Namely, the subsequent hexafluoropropylene oxide addition reaction may be carried out after converting the fluorinated alcohol to a metal alkoxide, and accordingly, such metal alkoxide may be employed as it is.

In a case where hexafluoropropylene oxide is added to the fluorinated alcohol (formula 4-2) to produce the fluorinated ether compound (formula 4-3), it is usual that the fluorinated alcohol is converted to a metal alkoxide, which is then reacted with hexafluoropropylene oxide. As the metal component of this metal alkoxide, an alkali metal or silver may, for example, be used. For example, in a solvent for reaction, the fluorinated alcohol is reacted with a basic alkali metal salt (such as potassium carbonate or sodium carbonate) at room temperature to obtain a metal alkoxide. Then, the obtained metal alkoxide is reacted with hexafluoropropylene oxide, without isolating it from the solvent for reaction or after isolating it and adding a new solvent for reaction. As the conditions for reacting hexafluoropropylene oxide, the same reaction conditions as in the case where hexafluoropropylene oxide is added to the above-mentioned fluorinated ketone compound (formula 3-3) to produce the fluorinated ether compound (formula 3-4), may be employed.

The pyrolysis of the fluorinated ether compound (formula 4-3) may be carried-out by the same method under the same reaction conditions as the pyrolysis of the above-mentioned fluorinated ether compound (formula 3-4). For example, it is possible to employ a method of pyrolyzing the fluorinated ether compound (formula 4-3) in a gas phase as mentioned above, or a method of converting the fluorinated ether compound (formula 4-3) to a salt of a carboxylic acid as mentioned above, followed by pyrolysis. It is also possible that as mentioned above, the fluorinated ether compound (formula 4-3) is converted to an alkyl ester of the corresponding carboxylic acid, which is then converted to a salt of the carboxylic acid, and this salt of the carboxylic acid is pyrolyzed.

The fluorinated diene represented by the formula 1 of the present invention, is polymerizable and is useful as a monomer for the production of a fluoropolymer. Such a fluorinated diene undergoes cyclopolymerization by an action of a radical polymerization initiator to form a polymer having monomer units having fluorinated alicyclic structures in its main chain. Further, it can be copolymerized with other monomers.

The copolymerizable other monomers are not particularly limited so long as they are radical polymerizable monomers, and a wide range of fluoromonomers, hydrocarbon monomers and other monomers, may be mentioned. Particularly preferred is an olefin such as ethylene, or a fluoroolefin such as tetrafluoroethylene. Further, a fluorinated vinyl ether type monomer such as a perfluoro(alkyl vinyl ether), a cyclopolymerizable fluorinated diene (other than the fluorinated diene represented by the formula 1) such as perfluoro (butenyl vinyl ether) or perfluoro(allyl vinyl ether) or a monomer having a fluorinated alicyclic structure such as perfluoro(2,2-dimethyl-1,3-dioxole), may, for example, be also copolymerizable. Such other monomers may be copolymerized with the fluorinated diene, alone or in combination of two or more of them.

The present invention also provides a homopolymer of the above-mentioned fluorinated diene of the present invention, or a copolymer of two or more of such fluorinated dienes, and a copolymer of the above-mentioned fluorinated diene of the present invention with other monomers copolymerizable therewith. The proportion of monomer units formed by polymerization of the fluorinated diene of the present invention in such polymers, is preferably from 30 to 100 mol %, particularly preferably from 50 to 100 mol %, based on the total monomer units. Further, the molecular weight is preferably from 500 to 100,000, particularly preferably from 500 to 10,000.

As the radical polymerization initiator, any polymerization initiator employed in usual radical polymerization, such as an azo compound, an organic peroxide or an inorganic peroxide, may be used. The following compounds may be mentioned as specific radical polymerization initiators. Diisopropyl peroxydicarbonate, an azo compound such as 2,2'-azobis(2-amidinopropane) dihydrochloride, 4,4'-azobis (4-cyanopentanoic acid), 2,2'-azobis(4-methoxy-2,4-dimethylvaleronitrile) or 1,1'-azobis(1-cyclohexane carbonitrile), an organic peroxide such as benzoyl peroxide, perfluoro benzoyl peroxide, perfluorononanoyl peroxide or methyl ethyl ketone peroxide, and an inorganic peroxide such as $K_2S_2O_8$ or $(NH_4)_2S_2O_8$.

The method for polymerization is also not particularly limited, and it may, for example, be so-called bulk polymerization wherein the fluorinated diene is directly subjected to polymerization, a solution polymerization which is carried out in a fluorohydrocarbon, a chlorinated hydrocarbon, a chlorinated fluorohydrocarbon, an alcohol, a hydrocarbon or other organic solvent, which is capable of dissolving the fluorinated diene, suspension polymerization which is carried out in an aqueous medium in the presence or absence of a suitable organic solvent, or emulsion polymerization which is carried out in an aqueous medium in the presence of an emulsifier. The temperature and the pressure for the polymerization are not particularly limited, but preferably suitably set taking into consideration various factors such as the boiling point of the fluorinated diene, the required heating source and removal of polymerization heat. For example, the polymerization temperature may be set at a suitable temperature within a range of from 0 to 200° C., particularly preferably from 30 to 100° C. Further, with respect to the polymerization pressure, the polymerization may be carried out under reduced pressure or elevated pressure, and practically, it can be carried out suitably at a level of from normal pressure to 10 MPa, further specifically from normal pressure to 5 MPa.

As characteristics of the polymer of the present invention, it may be mentioned that it is excellent in transparency, it has high elastic modulus, yield and breaking elongation and is tough and excellent in impact resistance, and it has a high glass transition temperature and high heat resistance. By virtue of such characteristics, the polymer of the present invention can be utilized as an optical resin material to be used for optical fiber, optical waveguide or optical transmitter such as a lens, which is excellent in heat resistance by itself. Further, the polymer of the present invention is characterized also in that it is optically transparent and has a refractive index lower than the conventional transparent fluororesin. For this reason, it may be combined with e.g. a conventional transparent fluororesin having a low refractive index, such as CYTOP (trade name, manufactured by Asahi Glass Company, Limited) or Teflon AF (trade name, manufactured by Dupont) to obtain an optical device such as optical fiber or optical waveguide excellent in optical transparency and having high performance.

Especially, a plastic optical fiber wherein a mixture having a refractive index raising agent mixed to the polymer of the present invention, is used as a core, and the polymer of the present invention is used as a clad, is excellent in heat resistance. Such plastic optical fiber may be of a step index type or a refractive index distribution type. The polymer of the present invention may suitably be employed for either type, but particularly suitable for a refractive index distribution type plastic optical fiber. As the above-mentioned refractive index raising agent, a fluorinated low molecular weight compound is preferred, since the transparency of the resulting mixture is thereby excellent. As such a fluorinated low molecular weight compound, perfluoro (triphenyltriazine), perfluoro(1,3,5-triphenylbenzene) or chlorotrifluoroethylene oligomer, may, for example, be mentioned as a preferred example. Further, a mixture of two or more of such compounds may be used as the refractive index raising agent.

The following methods may be mentioned as methods for producing the above-mentioned refractive index distribution type plastic optical fiber. A method wherein a cylindrical columnar molded product of the polymer of the present invention is produced wherein at the center axis portion a prescribed concentration of a refractive index raising agent is present, and the refractive index raising agent is diffused by thermodiffusion from the center axis portion in a radial direction to form a refractive index distribution, and then, the obtained cylindrical columnar molded product is used as a preform to form an optical fiber (JP-A-8-5848). A method wherein the polymer of the present invention is melt-extruded and formed into a fiber shape to form an optical fiber, whereby a highly concentrated refractive index raising agent is permitted to be present at the center axis portion, and the optical fiber is produced while thermally diffusing the refractive index raising agent (JP-A-8-5848). A method wherein a cylindrical tubular molded product is made of the polymer of the present invention, a predetermined amount of a refractive index raising agent is introduced to the center portion, followed by thermodiffusion to form a cylindrical tubular preform having a refractive index distribution, from which an optical fiber is formed (JP-A-8-334633).

Further, the polymer of the present invention is soluble in a fluorinated solvent such as perfluoro(2-butyltetrahydrofuran), perfluorooctane, perfluorohexane, perfluoro(tributylamine), perfluoro(tripropylamine), perfluorobenzene or dichloropentafluoropropane. A solution obtained by dissolving the polymer of the present invention in such a solvent, may be coated on a substrate such as a glass or a silicon wafer by spin coating or spraying, and then the solvent is evaporated and dried to form a thin film.

Further, with the polymer of the present invention, the terminal group may readily be substituted by e.g. heat treatment or fluorine gas treatment, and the adhesive property to various substrates may be modified by a treating method. For example, the polymer of the present invention may be heated at a temperature of at least 200° C. in the presence of air and then treated in water to introduce a carboxyl group to the terminal. Further, it may be reacted with fluorine gas to remove the terminal reactive functional group, whereby the thermal stability of the polymer can be improved.

EXAMPLES

Now, Examples of the present invention will be described. The present invention is by no means restricted to such Examples.

Example 1

Method for Synthesis of a Fluorinated Epoxide

Into a four necked glass flask having an internal capacity of 10 l, 6,330 g (13.0 mol) of a 15% sodium hypochlorite aqueous solution and 73.8 g of trioctylmethylammonium chloride were introduced, and while thoroughly stirring, cooled until the internal temperature became from 10 to 15° C. Then, 1,200 g (4.25 mol) of $CF_2ClCFClCF_2CF=CF_2$ synthesized by a method known by a literature, was dropwise added thereto, so that the internal temperature was maintained to be from 20 to 30° C. Then, while tracing the reaction by gas chromatograph, the reaction was carried out until $CF_2ClCFClCF_2CF=CF_2$ as the raw material was substantially consumed. By two phase separation, the product of the lower layer was withdrawn and washed three times with deionized water to remove the remaining sodium hypochlorite. The crude product was further distilled to obtain 828.7 g of a pure fluorinated epoxide represented by the following formula (1,2-dichloro-4,5-epoxy-1,1,2,3,3,4,5,5-octafluoropentane) (yield: 65%).

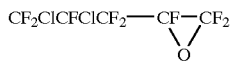

Example 2

Method for Synthesis of $CF_2ClCFClCF_2(C=O)CF_3$

Into a four necked glass flask having an internal capacity of 2 l, 35 g (0.26 mol) of aluminum chloride was introduced, and 70 g of trichlorofluoromethane was added to carry out activation. While thoroughly stirring, 1,470 g (4.93 mol) of the fluorinated epoxide synthesized in Example 1, was dropwise added thereto, so that the internal temperature was maintained to be from 20 to 30° C. Then, while tracing the reaction by gas chromatograph, the reaction was carried out at a reaction temperature of from 20 to 40° C. until the raw material was substantially consumed. Then, the crude product was isolated by filtration and subjected to distillation to obtain 1,600 g of pure $CF_2ClCFClCF_2(C=O)CF_3$ (4,5-dichloro-1,1,1,3,3,4,5,5-octafluoro-2-pentanone) (yield: 91%).

Example 3

Method for Synthesis of $CF_2ClCFClCF_2CF(CF_3)OCF(CF_3)COF$

Into a hastelloy alloy autoclave having an internal capacity of 2 l, 18 g (0.31 mol) of potassium fluoride was introduced, followed by vacuuming. Then, 1,150 g (3.86 mol) of $CF_2ClCFClCF_2(C=O)CF_3$ and 730 g of tetraglyme were introduced, followed by cooling with thorough stirring until the internal temperature became from 0 to 5° C., and stirring was continued at that temperature for from 30 minutes to 1 hour. Then, a cylinder of hexafluoropropylene oxide was connected, and while maintaining the internal pressure at about 0.2 MPa and the internal temperature at a level of at most 25° C., 640 g of hexafluoropropylene oxide was added. Thereafter, hexafluoropropylene oxide was purged, and then stirring was carried out at 25° C. for 1 to 2 hours. Then, the autoclave was opened, and the remaining solid was removed by filtration, and by phase separation, a crude product was taken out. The crude product was further distilled to obtain 1,440 g of pure $CF_2ClCFClCF_2CF(CF_3)OCF(CF_3)COF$ (6,7-dichloro-2,4-bis(trifluoromethyl)-2,4,5,5,6,7,7-heptafluoro-3-oxaheptanoic acid fluoride) (yield: 80%).

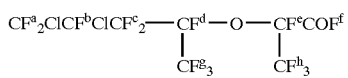

$^{19}$F-NMR(CDCl$_3$, CFCl$_3$ standard) δ ppm: −126.5 to −135.5 (F$^b$, F$^d$, F$^e$, 3F), −109 to −115.5 (F$^c$, 2F), −81.8 (F$^g$, 3F), −77 to −78.5 (F$^h$, 3F), −62.0 to −66.0 (F$^a$, 2F), 26.9 to 28.4 (F$^f$, 1F).

Boiling point: 68° C./5.3 kPa.

Example 4

Method for Synthesis of $CF_2ClCFClCF_2CF(CF_3)OCF=CF_2$

Into a four necked glass flask having an internal capacity of 2 l, 607 g (13.2 mol) of ethanol was introduced and cooled until the internal temperature became from 5 to 10° C. While thoroughly stirring and maintaining the internal temperature at from 5 to 20° C., 1,388 g (2.99 mol) of $CF_2ClCFClCF_2CF(CF_3)OCF(CF_3)COF$ was dropwise added. Thereafter, stirring was continued for a while at room temperature, and 720 g of deionized water was added, followed by thorough stirring. By two phase separation, the product of the lower layer was withdrawn. Then, this product was transferred to a glass separable flask having an internal capacity of 5 l and cooled until the internal temperature became from 5 to 10° C. While thoroughly stirring and maintaining the internal temperature at from 5 to 20° C., a 15% potassium hydroxide ethanol solution was dropwise added. Thereafter, ethanol as the solvent was distilled off under reduced pressure, and the obtained solid salt was pulverized by a mortar and then dried at 80° C. for two days in a vacuum dryer to obtain 1,480 g (2.96 mol) of $CF_2ClCFClCF_2CF(CF_3)OCF(CF_3)CO_2K$.

Then, into a four necked glass flask having an internal capacity of 2 l, 970 g (1.94 mol) of $CF_2ClCFClCF_2CF(CF_3)OCF(CF_3)CO_2K$ was introduced, and heated under vacuum until the internal temperature became from 190 to 200° C. to carry out a pyrolytic reaction. The product was recovered by a dry ice trap on a vacuum pump side the crude product was further distilled to obtain 688 g of pure $CF_2ClCFClCF_2CF(CF_3)OCF=CF_2$ (6,7-dichloro-1,1,2,4,5,5,6,7,7-nonafluoro-4-trifluoromethyl-3-oxa-1-pentene) (yield: 89%)

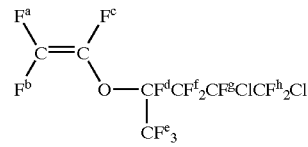

$^{19}$F-NMR(CDCl$_3$, CFCl$_3$ standard) δ ppm: −134.5 to −130.5 (F$^d$, F$^g$, 2F), −134.1 (F$^a$, 1F, J$_{ac}$=113 Hz), −121 (F$^c$, 1F, J$_{bc}$=166 Hz), −113.9 (F$^e$, 1F, J$_{ab}$=65 Hz), −111 to −115.5 (F$^f$, 2F), −78.1 (F$^e$, 3F), −62 to −65 (F$^h$, 2F)

Boiling point: 63° C./6.7 kPa.

Example 5

Synthesis of $CF_2=CFCF_2CF(CF_3)OCF=CF_2$

Into a four necked glass flask having an internal capacity of 2 l and equipped with a stirrer, a reflux condenser and a dropping funnel, 207 g (3.17 mol) of zinc was introduced, and in an inert gas atmosphere, 975 g of dimethylformamide was introduced. Then, the system was vacuumed to 27 kPa, and further, the internal temperature was adjusted to from 55 to 60° C., whereupon 516 g (1.27 mol) of $CF_2ClCFClCF_2CF(CF_3)OCF=CF_2$ was dropwise added slowly from the dropping funnel. During the reaction, the product was distilled and thereby quickly withdrawn. Thereafter, the crude product was rectified to obtain 348 g of pure $CF_2=CFCF_2CF(CF_3)OCF=CF_2$ (1,1,2,4,5,5,6,7,7-nonafluoro-4-trifluoromethyl-3-oxa-1,6-pentadiene) (yield: 84%).

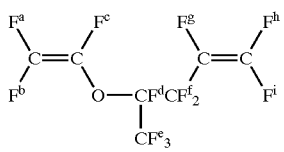

$^{19}$F-NMR(CDCl$_3$, CFCl$_3$ standard) δ ppm: −187.3 (F$^g$, 1F, J$_{gh}$=39 Hz), −140.7 (F$^d$, 1F), −132.7 (F$^c$, 1F), −121.1 (F$^b$, 1F, J$_{bc}$=111 Hz), −117.4 (F$^f$, 2F), −113.5 (F$^a$, 1F, J$_{ab}$=83 Hz, J$_{ac}$=65 Hz), −104.2 (F$^i$, 1F, J$_{gi}$=116 Hz), −87.7 (F$^h$, 1F, J$_{hi}$=50 Hz), −78.9 (F$^e$, 3F).

IR: 1,785 cm$^{-1}$ (CF$_2$=CF—), 1,835 cm$^{-1}$ (CF$_2$=CFO—)

Boiling point: 54.5° C./33.3 kPa.

Example 6

Method for Synthesis of CF$_2$ClCFClCF$_2$C(CF$_3$)$_2$OH

Into a four necked glass flask having an internal capacity of 5 l and equipped with a stirrer, a dropping funnel and three-way stopcock, 134 g (2.3 mol) of potassium fluoride was introduced, and in an inert gas atmosphere, 1,500 ml of tetrahydrofuran was introduced. Then, the internal temperature was adjusted to −78° C., whereupon 200 g (0.8 mol) of CF$_2$ClCFClCF$_2$COF synthesized by a method known by a literature and 265 g (1.86 mol) of trifluoromethyl trimethylsilane, were dropwise added thereto. Then, the internal temperature was slowly raised to 0° C., and the reaction was carried out at 0° C. for 12 hours.

After the reaction, the solvent and low boiling products were distilled off under reduced pressure, and the organic component in the remaining solid was extracted with diethyl ether. Further, the diethyl ether was distilled off under reduced pressure. The main component of the remaining brown solid was CF$_2$ClCFClCF$_2$C(CF$_3$)$_2$OK, and the yield of the formed solid was 220 g.

To 220 g of the obtained solid, 200 ml of concentrated sulfuric acid was slowly dropwise added under cooling with ice, and stirring was continued for from 1 to 2 hours at room temperature. Then, the reaction solution was slowly poured into 500 ml of water cooled with ice, followed by extraction with diethyl ether. The organic layer was separated and then dried over magnesium sulfate. Diethyl ether was distilled off under reduced pressure. A crude product thus obtained was purified by distillation to obtain 89 g of CF$_2$ClCFClCF$_2$C(CF$_3$)$_2$OH (yield: 30%, based on CF$_2$ClCFClCF$_2$COF)

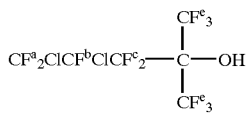

$^{19}$F-NMR(CDCl$_3$, CFCl$_3$ standard) δ ppm: −131.9 (F$^b$, 1F), −107.5 (F$^c$, 2F), −72.4 and −71.9 (F$^e$, each 3F), −63.2 (F$^a$, 2F).

Example 7

Method for Synthesis of CF$_2$ClCFClCF$_2$C(CF$_3$)$_2$OCF(CF$_3$) CO$_2$CH$_3$

Into a four necked glass flask having an internal capacity of 200 ml equipped with a stirrer, a reflux condenser and a dropping funnel, 59 g (181 mmol) of cesium carbonate and 110 ml of dimethoxyethane were introduced and thoroughly stirred in an inert gas atmosphere. While maintaining the internal temperature at from 0 to 10° C., 44.5 g (121 mmol) of CF$_2$ClCFClCF$_2$C(CF$_3$)$_2$OH was dropwise added. After completion of the dropwise addition, stirring was continued for 4 hours at an internal temperature of 25° C. Then, the solvent was distilled off under reduced pressure to obtain a brown solid salt CF$_2$ClCFClCF$_2$C(CF$_3$)$_2$OCs, Then, CF$_2$ClCFClCF$_2$C(CF$_3$)$_2$OCs was dissolved in 160 ml of acetonitrile, and the solution was put into a hastelloy alloy autoclave having an internal capacity of 200 ml and vacuumed, and while thoroughly stirring, cooled until the internal temperature became from 0 to 5° C. Then, a cylinder of hexafluoropropylene oxide is connected, and while maintaining the internal pressure at about 0.2 MPa and the internal temperature at a level of at most 25° C., 29.5 g (178 mmol) of hexafluoropropylene oxide was added. Thereafter, stirring was continued for one hour at from 0 to 5° C. and for from 1 to 2 hours at 30° C. Then, the autoclave was opened, and the remaining solid was removed by filtration, and by phase separation, a crude product was taken out. This product was a mixture of products which were CF$_2$ClCFClCF$_2$C(CF$_3$)$_2$OCF(CF$_3$)COF and CF$_2$ClCFClCF$_2$C(CF$_3$)$_2$OCF(CF$_3$)CO$_2$C(CF$_3$)$_2$CF$_2$CFClCF$_2$Cl. This product was treated with methanol in the presence of potassium fluoride and extracted with a dichloropentafluoropropane solvent (hereinafter referred to as R225)-water system. The organic layer was separated and then dehydrated over magnesium sulfate, followed by distillation of the solvent to obtain a crude product. The crude product was further distilled to remove low boiling impurities to obtain 30 g of pure CF$_2$ClCFClCF$_2$C(CF$_3$)$_2$OCF(CF$_3$)CO$_2$CH$_3$ (methyl 6,7-dichloro-2,4,4-tristrifluoromethyl-2,5,5,6,7,7-hexafluoro-3-oxaheptanoate) (yield: 47%).

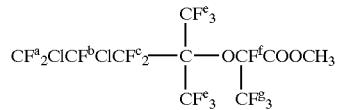

$^{19}$F-NMR(CDCl$_3$, CFCl$_3$ standard) δ ppm: −133 to −129.5 (F$^b$ and F$^t$, 2F), −110 to −97 (F$^c$, 2F), −82.1 (F$^g$, 3F), −66.9 and −65.9 (F$^e$, each 3F), −65.0 to −62.5 (F$^a$, 2F)

$^1$H-NMR (CDCl$_3$, Si(CH$_3$)$_4$ standard) δ ppm: 3.95 (3H)

Example 8

Method for Synthesis of CF$_2$ClCFClCF$_2$C(CF$_3$)$_2$OCF=CF$_2$

Into a glass separable flask having an internal capacity of 200 ml and equipped with a stirrer, a reflux condenser and a dropping funnel, 28 g (53 mmol) of CF$_2$ClCFClCF$_2$C(CF$_3$)$_2$OCF(CF$_3$) CO$_2$CH$_3$ was introduced, and cooled until the internal temperature became from 5 to 10° C., and while thoroughly stirring and maintaining the internal temperature at from 5 to 20° C., 20 g of a 15% potassium hydroxide ethanol solution, was dropwise added. Thereafter, ethanol as the solvent was distilled off under reduced pressure, and the obtained solid salt was pulverized by a mortar and dried for two days at 80° C. in a vacuum dryer to obtain 27.5 g (50 mmol) of CF$_2$ClCFClCF$_2$C(CF$_3$)$_2$OCF (CF$_3$) CO$_2$K.

Then, into a three necked glass flask having an internal capacity of 100 ml, 15 g (27 mmol) of CF$_2$ClCFClCF$_2$C(CF$_3$)$_2$OCF(CF$_3$)CO$_2$K was introduced and heated under vacuum until the internal temperature became from 150 to 170° C. for a pyrolytic reaction. The product was recovered by a dry ice trap on a vacuum pump side. The crude product was further distilled to obtain 3.7 g of pure CF$_2$ClCFClCF$_2$C(CF$_3$)$_2$OCF=CF$_2$ (6,7-dichloro-1,1,2,5,5,6,7,7-octafluoro-4,4'-bis(trifluoromethyl)-3-oxa-1-pentene) (yield: 30%).

Further, it is considered possible to synthesize CF$_2$=CFCF$_2$C(CF$_3$)$_2$OCF=CF$_2$ by dechlorinating the product in the same manner as in Example 3.

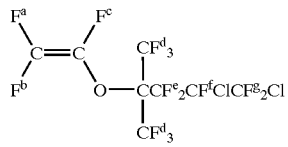

$^{19}$F-NMR(CDCl$_3$, CFCl$_3$ standard) δ ppm; -131.7 (F$^a$, 1F, J$_{ac}$=83 Hz), -131.5 (F$^f$, 1F), -119.6 (F$^c$, 1F, J$_{bc}$=111 Hz), -114.8 (F$^b$, 1F, J$_{ac}$=65 Hz), -110 to -100 (F$^e$, 2F), -68.0 and -67.6 (F$^d$, each 3F), -65.0 and -62.0 (F$^g$, 2F).

Boiling point: 63° C./2.7 kPa.

Example 9

Polymerization of CF$_2$=CFCF$_2$CF(CF$_3$)OCF=CF$_2$ 2 g of CF$_2$=CFCF$_2$CF(CF$_3$)OCF=CF$_2$ and 6.2 mg of diisopropyl peroxydicarbonate were put into a glass ampoule, frozen in liquid nitrogen, vacuum-deaerated and then sealed. After heating at 40° C. for 20 hours in an oven, the solidified content was taken out and dried at 200° C. for one hour. The yield of the obtained polymer (hereinafter referred to as polymer A1) was 99%. A part of polymer A1 was dissolved in perfluoro(2-butyltetra hydrofuran) (hereinafter referred to as PBTHF), and the intrinsic viscosity was measured and found to be 0.44 dl/g. The molecular weight of the polymer was 131,500 as the number average molecular weight (Mn) and 263,000 as the weight average molecular weight (Mw).

A film of polymer A1 prepared by press-molding had a refractive index of 1.327 as measured by an Abbe refractometer and a glass transition temperature of 124° C. as measured by a dynamic thermomechanical analysis (DMA). The tensile properties of polymer A1 were measured, whereby the tensile modulus was 1,430 MPa, the yield stress was 36 MPa and the breaking elongation was 4.2%. Further, the zero shear viscosity was measured at 230° C. by a rotational melt viscoelasticity measuring apparatus and found to be 89,000 Pa.s. The glass transition temperature of the polymer obtained by polymerizing monomer CF$_2$=CFCF$_2$CF$_2$OCF=CF$_2$ (perfluoro butenyl vinyl ether "hereinafter referred to as PBVE") under the same condition, was 108° C. as measured by a dynamic thermomechanical analysis (DMA), whereby with the present polymer A1, an improvement in the glass transition temperature was confirmed as compared with the conventional resin.

Further, the infrared absorption spectrum of the polymer was measured, whereby the absorptions at 1,785 cm$^{-1}$ attributable to CF$_2$=CF— and at 1,835 cm$^{-1}$ attributable to CF$_2$=CFO—, which were observed with the monomer, were found to have been diminished. This polymer A1 had no pendant double bond and underwent no crosslinking reaction, and it was found to be a cyclized polymer, since it can be completely dissolved in R225 (dichloropentafluoropropane) even at a high conversion. Further, it was found to be a polymer having repeating units having the following structure, by the $^{19}$F-NMR analysis.

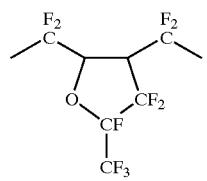

Example 10

2 g of CF$_2$=CFCF$_2$CF(CF$_3$)OCF=CF$_2$ and 5.0 mg of perfluoro benzoyl peroxide were put into a glass ampoule, frozen in liquid nitrogen, vacuum-deaerated and then sealed. After heating at 70° C. for 20 hours in an oven, the solidified content was taken out and vacuum-dried at 100° C. for 10 hours. The yield of the obtained polymer (hereinafter referred to as polymer A2) was 96%. A part of polymer A2 was dissolved in PBTHF, and the intrinsic viscosity was measured and found to be 0.77 dl/g. A film of polymer A2 prepared by press-molding had a refractive index of 1.329 as measured by an Abbe refractometer and a glass transition temperature of 124° C. as measured by a dynamic thermo-mechanical analysis (DMA). The tensile properties of polymer A2 were measured, whereby the tensile modulus was 1,370 MPa, the yield stress was 38 MPa, and the breaking elongation was 7.0%. Further, the polymer of CF$_2$=CFCF$_2$CF(CF$_3$)OCF=CF$_2$ was excellent in transparency and found to be useful as an optical resin material for e.g. optical fiber or optical waveguide.

Example 11

Into a stainless steel autoclave having an internal capacity of 200 ml, 80 g of water, 15 g (45.7 mmol) of CF$_2$=CFCF$_2$CF(CF$_3$)OCF=CF$_2$, 38 mg of perfluoro benzoyl peroxide and 2.4 g of methanol were introduced. The autoclave was flushed with nitrogen and then heated until the internal temperature of the autoclave became 70° C., whereupon polymerization was carried out for 20 hours. The obtained polymer was washed with deionized water and methanol and then dried at 200° C. for one hour. The yield of the obtained polymer (hereinafter referred to as polymer A3) was 83%.

A part of polymer A3 was dissolved in PBTHF, and the intrinsic viscosity was measured and found to be 0.31 dl/g. A film of polymer A3 prepared by press molding had a refractive index of 1.328 as measured by an Abbe refractometer and a glass transition temperature of 124° C. as measured by a differential scanning calorimetory (DSC). The tensile properties of polymer A3 were measured, whereby the tensile modulus was 1,280 MPa, the yield stress was 38 MPa, and the breaking elongation was 5.1%. Further, the zero shear viscosity was measured at 230° C. by a rotational melt viscoelasticity measuring apparatus and found to be 5,200 Pa.s.

Example 12

Copolymerization of CF$_2$=CFCF$_2$CF(CF$_3$)OCF=CF$_2$ with Tetrafluoroethylene Into a stainless steel autoclave having an internal capacity of 200 ml, 80 ml of R225, 5.6 g (17 mmol) of CF$_2$=CFCF$_2$CF(CF$_3$)OCF=CF$_2$ and 0.025 g of perfluoro benzoic peroxide were introduced. The autoclave was vacuumed by a vacuum pump while being cooled with liquid nitrogen, then the vacuum pump was disconnected to let the temperature return to room temperature, and then the autoclave was again vacuumed by a vacuum pump while being cooled with liquid nitrogen. This operation was repeated three times. Then, the internal temperature of the autoclave was returned to room temperature, and then 32 g (320 mmol) of tetrafluoroethylene was introduced. And, the autoclave was heated until the internal temperature became 70° C., and polymerization was carried out for 3 hours. Then, the remaining tetrafluoroethylene was purged, and the remaining monomer was distilled off under reduced pressure, to obtain 30 g of a white polymer (hereinafter referred to as polymer B1). The structure of the obtained polymer B1 was analyzed, whereby it was found that the structure derived from $CF_2=CFCF_2CF(CF_3)OCF=CF_2$ was introduced in an amount of 2 mol % to a part of polytetrafluoroethylene.

Example 13

Copolymer of $CF_2=CFCF_2CF(CF_3)OCF=CF_2$ with PBVE

Into a stainless steel autoclave having an internal capacity of 200 ml, 80 g of water, 15 g of $CF_2=CFCF_2CF(CF_3)OCF=CF_2$, 15 g of PBVE, 75 mg of perfluoro benzoyl peroxide and 2.4 g of methanol were introduced. The autoclave was flushed with nitrogen and then heated until the internal temperature of the autoclave became 70° C., whereupon polymerization was carried out for 20 hours. The obtained polymer (hereinafter referred to as polymer B2) was washed with deionized water and methanol and then dried at 200° C. for one hour. The yield of the obtained polymer B2 was 85%.

A part of polymer B2 was dissolved in PBTHF, and the intrinsic viscosity was measured and found to be 0.35 dl/g. A film of polymer B2 prepared by press molding had a refractive index of 1.336 as measured by an Abbe refractometer and a glass transition temperature of 116° C. as measured by a dynamic thermomechanical analysis (DMA).

Example 14

Copolymerization of $CF_2=CFCF_2CF(CF_3)OCF=CF_2$ with perfluoro(2,2-dimethyl-1,3-dioxole)

Into a stainless steel autoclave having an internal capacity of 200 ml, 80 g of water, 21 g of $CF_2=CFCF_2CF(CF_3)OCF=CF_2$, 9 g of perfluoro(2,2-dimethyl-1,3-dioxole) (hereinafter referred to as "PDD"), 75 mg of diisopropyl peroxydicarbonate and 2.4 g of methanol were introduced. The autoclave was flushed with nitrogen and then heated until the internal temperature of the autoclave became 40° C., whereupon polymerization was carried out for 20 hours. The obtained polymer (hereinafter referred to as polymer B3) was washed with deionized water and methanol and then dried at 200° C. for one hour. The yield of the obtained polymer B3 was 90%.

A part of polymer B3 was dissolved in PBTHF, and the intrinsic viscosity was measured and found to be 0.40 dl/g. A film of polymer B3 prepared by press molding had a refractive index of 1.315 as measured by an Abbe refractometer and a glass transition temperature of 167° C. as measured by a dynamic thermomechanical analysis (DMA).

Example 15

93 parts of polymer A1 obtained in Example 9 and 7 parts of perfluoro(triphenyltriazine) were put into a glass ampoule, sealed and then uniformly melt-mixed at 240° C. to obtain a polymer mixture (hereinafter referred to as mixture C1). A film of mixture C1 prepared by press molding had a refractive index of 1.349 as measured by an Abbe refractometer and a glass transition temperature of 102° C. as measured by a dynamic thermomechanical analysis (DMA).

Then, in accordance with the method disclosed in JP-A-8-5848, an optical fiber was prepared by using mixture C1 and polymer A1. Namely, firstly, mixture C1 was melted in a sealed glass tube to obtain a cylindrical columnar molded product C1a. Then, a cylindrical tube was melt-molded solely by polymer A1, and into the hollow portion of this cylindrical tube, molded product C1a was inserted and heated at 220° C. for integration to obtain a preform. This preform was melt-spun at 240° C. to obtain an optical fiber wherein the refractive index gradually decreased from the center portion towards the peripheral portion.

The attenuation of the obtained optical fiber was measured by a cutback method and found to be 192 dB/km at 650 nm, 109 dB/km at 850 nm and 81 dB/km at 1,300 nm, whereby it was confirmed to be an optical fiber capable of excellently transmitting light ranging from visible light to near infrared light.

This optical fiber was heated and stored in an oven of 70° C. for 10,000 hours and then withdrawn, whereupon the refractive index distribution was measured by an interface interference microscope and compared with the refractive index distribution before the heat storage, whereby no change was observed. Further, the bandwidth was measured by a pulse method to evaluate the transmission characteristics. The bandwidth was measured after heating and storing the optical fiber at 70° C. for 10,000 hours, whereby it was 360 MHz.km both before and after the heat storage, and no decrease of the bandwidth took place, whereby it was confirmed that the heat resistance was excellent.

Example 16

By means of an extruder, an optical fiber of a core-clad type was spun by carrying out two-color extrusion concentrically so that the polymer of PBVE (intrinsic viscosity: 0.27 dl/g, refractive index: 1.342) was located at the center portion and polymer A3 was located at the peripheral portion. The outer diameter of the obtained optical fiber was 510 μm, and the core diameter was 490 μm. Further, the attenuation was measured by a cutback method and found to be 146 dB/km at 650 nm, 85 dB/km at 850 nm and 71 dB/km at 1,300 nm, whereby it was confirmed to be an optical fiber capable of excellently transmitting light ranging from visible light to near infrared light.

Example 17

The preform obtained in Example 15 was further covered with a hollow tube made of polymer B3, followed by melt spinning at 240° C. to obtain an optical fiber in which the refractive index gradually decreased from the center portion towards the peripheral portion. The attenuation of the obtained optical fiber was measured by a cutback method and found to be 142 dB/km at 650 nm, 59 dB/km at 850 nm and 31 dB/km at 1,300 nm, whereby it was confirmed to be an optical fiber capable of excellently transmitting light ranging from visible light to near infrared light. Further, the increase in attenuation at a bending radius of 10 mm of this optical fiber was measured at 850 nm and found to be 0.13 dB, whereby it was found to be an optical fiber having a small bending loss.

This optical fiber was heated and stored in an oven of 70° C. for 10,000 hours, and then, the attenuation was measured, whereby no change was observed. Further, the bandwidth was measured by a pulse method to evaluate the transmission characteristics. The bandwidth was measured after heating and storing the optical fiber at 70° C. for 10,000 hours, whereby it was 280 MHz.km both before and after the heat storage, and no decrease of the bandwidth took place, whereby it was confirmed that the heat resistance was good.

Example 18

PDD and tetrafluoroethylene were subjected to radical polymerization in a mass ratio of 80:20 by using PBTHF as a solvent to obtain a polymer having a Tg of 160° C. and a number average molecular weight of about $1.7 \times 10^5$. This polymer was heat-treated at 250° C. for 5 hours in an atmosphere of a fluorine/nitrogen mixed gas (fluorine gas concentration: 20 vol. %) to obtain a polymer (hereinafter referred to as polymer D1) having good light transmittance and heat stability. Polymer D1 is colorless and transparent, and its refractive index was 1.305.

Example 19

By means of an extruder, an optical fiber of a core-clad type was spun by carrying out two-color extrusion concentrically so that polymer A1 was located at the center portion and polymer D1 was located at the peripheral portion. The outer diameter of the obtained optical fiber was 980 μm, and the core diameter was 900 μm. Further, the attenuation was measured by a cutback method and found to be 186 dB/km at 650 nm, 95 dB/km at 850 nm and 71 dB/km at 1,300 nm, whereby it was confirmed to be an optical fiber capable of excellently transmitting light ranging from visible light to near infrared light.

Example 20

92.5 parts of polymer A1 and 7.5 parts of perfluoro(1,3, 5-triphenylbenzene) were put into a glass ampoule, sealed and then uniformly melt-mixed at 250° C. to obtain a polymer mixture (hereinafter referred to as mixture C2). A film of mixture C2 prepared by press molding, had a refractive index of 1.358 as measured by an Abbe refractometer and a glass transition temperature of 98° C. as measured by a dynamic thermomechanical analysis (DMA).

Then, an optical fiber was produced by using mixture C2 and polymer A1. Namely, firstly, mixture C2 was melted in a sealed glass tube to obtain a cylindrical columnar molded product C2a. Then, a cylindrical tube was melt-molded solely by polymer A1, and into the hollow portion of this cylindrical tube, the molded product C2a was inserted and heated to 220° C. for integration to obtain a preform. This preform was melt-spun at 240° C. to obtain an optical fiber wherein the refractive index gradually decreased from the center portion to the peripheral portion.

The attenuation of the obtained fiber was measured by a cutback method and found to be 180 dB/km at 650 nm, 92 dB/km at 850 nm and 80 dB/km at 1,300 nm, whereby it was confirmed to be an optical fiber capable of excellently transmitting light ranging from visible light to near infrared light.

This optical fiber was heated and stored in an oven of 70° C. for 2,000 hours and then withdrawn, whereupon the refractive index distribution was measured by an Interfaco interference microscope and compared with the refractive index distribution before the heat storage, whereby no change was observed. Further, the bandwidth was measured by a pulse method to evaluate the transmission characteristics. The bandwidth was measured after heating and storing the optical fiber at 70° C. for 2,000 hours, whereby it was 320 MHz-km both before and after the heat storage, and no decrease in the bandwidth took place, whereby it was confirmed that the heat resistance was good.

Example 21

85 parts of polymer A1 and 15 parts of chlorotrifluoroethylene oligomer were put into a glass ampoule, sealed and then uniformly melt-mixed at 250° C. to obtain a polymer mixture (hereinafter referred to as mixture C3). A film of mixture C3 prepared by press molding, had a refractive index of 1.356 as measured by an Abbe refractometer and a glass transition temperature of 90° C. as measured by a dynamic thermomechanical analysis (DMA).

Then, an optical fiber was prepared by using mixture C3 and polymer A1. Namely, firstly, mixture C3 was melted in a sealed glass tube to obtain a cylindrical columnar molded product C3a. Then, a cylindrical tube was melt-molded solely by polymer A1, and into the hollow portion of this cylindrical tube, the molded product C3a was inserted and heated to 220° C. for integration to obtain a preform. This preform was melt-spun at 240° C. to obtain an optical fiber wherein the refractive index gradually decreased from the center portion towards the peripheral portion.

The attenuation of the obtained optical fiber was measured by a cutback method and found to be 120 dB/km at 650 nm, 68 dB/km at 850 nm and 50 dB/km at 1,300 nm, whereby it was confirmed to be an optical fiber capable of excellently transmitting light ranging from visible light to near infrared light.

This optical fiber was heated and stored in an oven of 70° C. for 1,000 hours and then withdrawn, whereupon the refractive index distribution was measured by an interfaco interference microscope and compared with the refractive index distribution before the heat storage, whereby no change was observed. Further, the bandwidth was measured by a pulse method to evaluate the transmission characteristics. The bandwidth was measured after heating and storing the optical fiber at 70° C. for 1,000 hours, whereby it was 330 MHz.km both before and after the heat storage, and no decrease of the bandwidth took place, whereby it was confirmed that the heat resistance was good.

INDUSTRIAL APPLICABILITY

As compared with the conventional polymer of a fluorinated diene having no side chain, the polymer of the present invention has a high glass transition temperature and equal or higher optical properties such as transparency. Accordingly, the polymer of the present invention is useful as an optical resin material excellent in heat resistance, and it is a resin material having excellent properties particularly as a material for a plastic optical fiber.

The entire disclosure of Japanese Patent Application No. 2000-161714 filed on May 31, 2000 including specification, claims and summary is incorporated herein by reference in its entirety.

What is claimed is:

1. A fluorinated diene represented by the formula 1:

$$CF_2=CF(CF_2)_nC(CF_3)ROCF=CF_2 \qquad \text{Formula 1}$$

wherein R is a fluorine atom or a trifluoromethyl group, and n is an integer of from 1 to 3.

2. A method for producing a fluorinated diene represented by the formula 1, which comprises dehalogenating $Z^1$ and $Z^2$ of a fluorinated compound represented by the formula 2:

$$CF_2=CF(CF_2)_nC(CF_3)ROCF=CF_2 \qquad \text{Formula 1}$$

$$CF_2Z^1CFZ^2(CF_2)_nC(CF_3)ROCF=CF_2 \qquad \text{Formula 2}$$

wherein R is a fluorine atom or a trifluoromethyl group, each of $Z^1$ and $Z^2$ which are independent of each other, is a halogen atom other than a fluorine atom, and n is an integer of from 1 to 3.

3. A polymer comprising monomer units formed by polymerization of a fluorinated diene represented by the formula 1:

$$CF_2=CF(CF_2)_nC(CF_3)ROCF=CF_2 \qquad \text{Formula 1}$$

wherein R is a fluorine atom or a trifluoromethyl group, and n is an integer of from 1 to 3.

4. The polymer according to claim 3, wherein the monomer units of the fluorinated diene are monomer units having a ring structure formed by cyclopolymerization of the fluorinated diene represented by the formula 1.

5. The polymer according to claim 3, which is a copolymer obtained by copolymerizing a fluorinated diene represented by the formula 1 with at least one member selected from the group consisting of a cyclopolymerizable fluorinated diene other than the fluorinated diene represented by the formula 1, a monomer having a fluorinated alicyclic structure, a fluorinated vinyl ether monomer and a fluoroolefin:

$$CF_2=CF(CF_2)_nC(CF_3)ROCF=CF_2 \qquad \text{Formula 1}$$

wherein R is a fluorine atom or a trifluoromethyl group, and n is an integer of from 1 to 3.

6. The polymer according to claim 5, wherein the copolymer is a copolymer obtained by copolymerizing a fluorinated diene represented by the formula 1 with at least one member selected from the group consisting of tetrafluoroethylene, perfluoro(butenyl vinyl ether) and perfluoro(2,2-dimethyl-1,3-dioxol).

7. An optical transmitter employing the polymer as defined in claim 3.

8. A plastic optical fiber having a core containing a fluorinated low molecular weight compound as a refractive index raising agent in the polymer as defined in claim 3.

9. The plastic optical fiber according to claim 8, wherein the fluorinated low molecular weight compound as a refractive index raising agent is at least one member selected from the group consisting of perfluoro(triphenyltriazine), perfluoro(1,3,5-triphenylbenzene) and a chlorotrifluoroethylene oligomer.

10. The plastic optical fiber according to claim 8, wherein the plastic optical fiber is a refractive index distribution optical fiber.

* * * * *